US006187575B1

(12) United States Patent
Sobek et al.

(10) Patent No.: US 6,187,575 B1
(45) Date of Patent: Feb. 13, 2001

(54) THERMOLABILE URACIL-DNA-GLYCOSYLAS, PROCESS FOR ITS PREPARATION AND USE FOR REMOVING URACIL FROM DNA

(75) Inventors: Harald Sobek; Manfred Schmidt; Bruno Frey, all of Penzberg; Klaus Kaluza, Bad Heilbrunn, all of (DE)

(73) Assignee: Roche Diagnostics GmbH, Mannheim (DE)

( * ) Notice: Under 35 U.S.C. 154(b), the term of this patent shall be extended for 0 days.

(21) Appl. No.: 09/077,312

(22) PCT Filed: Dec. 4, 1996

(86) PCT No.: PCT/EP96/05398

§ 371 Date: Aug. 6, 1998

§ 102(e) Date: Aug. 6, 1998

(87) PCT Pub. No.: WO97/20922

PCT Pub. Date: Jun. 12, 1997

(30) Foreign Application Priority Data

Dec. 5, 1995 (DE) .............................................. 195 45 320

(51) Int. Cl.[7] ....................................................... C12N 9/14

(52) U.S. Cl. ........................ 435/200; 435/195; 435/91.21; 435/91.2; 435/91.1

(58) Field of Search .................................. 435/91.1, 91.2, 435/91.21, 195, 200

(56) References Cited

FOREIGN PATENT DOCUMENTS

WO 92/01814 * 2/1992 (WO) .

OTHER PUBLICATIONS

Leblanc et al, J. Biol. Chem. 257(7): 3477–3483, 1982.*
Chemical Absracts 98: 175974, 1983.*

* cited by examiner

Primary Examiner—Francisco Prats
(74) Attorney, Agent, or Firm—Arent Fox Kintner Plotkin & Kahn, PLLC

(57) ABSTRACT

Thermolabile enzyme with uracil-DNA-glycosylase activity which is in particular characterized by a high degree of purity, short half-lives and a content of contaminating foreign activities of less than 2%, a process for its isolation as well as the use thereof to remove the base uracil from DNA and in particular from PCR products containing uracil. The enzyme is obtainable from gram-positive microorganisms such as e.g. Arthrobacter or Micrococcus.

30 Claims, 3 Drawing Sheets

THERMOLABILE URACIL-DNA-GLYCOSYLAS, PROCESS FOR ITS PREPARATION AND USE FOR REMOVING URACIL FROM DNA

The invention concerns a thermolabile (heat labile) enzyme with uracil-DNA-glycosylase activity, a process for isolating the enzyme from gram-positive microorganisms and an improved method for the detection or removal of uracil from DNA containing uracil in particular from DNA fragments that are obtained after specific amplification (e.g. PCR).

Uracil-DNA-glycosylases (UNG; EC 3.2.2.3) are widespread, highly conserved and extremely specific DNA repair enzymes. Their biological function is to specifically remove the base uracil from DNA. Uracil can form in DNA by the spontaneous deamination of cytosine or by the misincorporation of dUTP during DNA synthesis. The deamination of cytosine leads to promutagenic U:G mismatches which, if not corrected, lead to transition mutations in the next cycle of DNA synthesis (Lindahl, T. (1993) Nature 362, 709–715).

UNGs are used especially within the framework of PCR technology to decontaminate PCR mixtures. The so-called carry-over contamination of PCR mixtures by amplified target-DNA can lead to false-positive results. Carry-over contamination can be kept under control by incorporating dUTP into all PCR products (whereby dTTP is replaced by dUTP) and treating ready-mixed PCR reactions with UNG followed by thermal inactivation of UNG. In this process UNG cleaves uracil from all DNAs containing uracil but has no effect on natural (i.e. target) DNA. The a basic sites which are formed block the replication of DNA by DNA polymerases. This carry-over prevention technology prevents PCR products from resulting PCRs from causing false-positive results by contamination (Longo et al. (1990) Gene 93, 125–128). UNG from *E. coli* is usually used for this method (WO 92/0181, EP 0 415 755). The corresponding use of UNGs for isothermal amplification is also described (EP 0 624 643).

Most of the UNGs known today have an adequately high specificity for the efficient cleavage of uracil from single-stranded and double-stranded DNA and can thus in principle be used to optimize specific amplification methods. In contrast the UNGs do not show any activity towards other "normal" DNA bases or towards uracil in RNA.

A series of UNGs isolated from prokaryotic and eukaryotic organisms as well as some of viral origin have been described. Microbial UNGs are in particular known from *E. coli* (T. Lindahl, PNAS 71 (9), 3649–3653 (1974); Lindahl et al., J. Biol. Chem. 252 (10), 3286–3294 (1977)), *Bacillus subtilis* (Cone et al., Biochemistry 16 (14), 3194–3201 (1977)), *Bacillus stearothermophilus* (Kaboev et al., FEBS Letters 132 (2), 337–340 (1981)), *Thermothrix thiopara* (Kaboev et al., J. Bacteriology 164 (1), 421–424 (1985)) and *Micrococcus luteus* (Leblanc et al., J. Biol. Chem. 257 (7), 3477–3483 (1982). In addition a UNG from humans (Krokan et al., Nucl. Acid Res. 9 (11), 2599–2613 (1981) and some UNGs of viral origin have been described. Moreover the structural basis for the specificity and catalysis of UNG has recently been elucidated (Savva et al., Nature 373, 487–493; Mol et al., Cell 80, 869–878 (1995)).

However, most UNGs do not meet the requirements for use as a carry-over prevention method for amplification methods such as e.g. PCR due to their inadequate degree of purity and other properties especially their thermolability that is too low. Thus even after drastic heat treatment such as for example 10 minutes, 95° C. and subsequent PCR a residual activity of UNG is still detected (Thornton et al., Bio Techniques 13 (2), 180–183 (1992)). The residual activity of UNG i.e. the continued degradation of PCR products containing uracil is usually prevented by further incubating the corresponding mixtures after the PCR reaction at high temperatures of about 70° to 72° C. Moreover it was observed that storage of the PCR mixture/PCR product even at ca 4° C. often leads to a further degradation of the PCR product. Therefore much lower temperatures such as ca. −20° C. are recommended for the storage and/or the inhibition of the residual activity of UNG by the addition of chloroform or phenol. In addition the search for more suitable heat labile mutants has not yet been successful (Duncan et al., J. Bacteriology 134, (3), 1039–1045 (1978); WO 92/01814).

Thus the activity of the UNGs that are presently available cannot be completely switched off or only by using additional measures which additionally complicate the entire process.

Therefore the object of the present invention was to provide an enzyme with uracil-DNA-glycosylase activity which enables the difficulties known from the state of the art in removing uracil from DNA to be largely solved or avoided.

The object is achieved by a thermolabile enzyme with uracil-DNA-glycosylase activity which is obtainable from gram-positive microorganisms with a degree of purity of at least 95% (SDS-gel) and by a half-life of less than 5 minutes at 40° C. and of approximately or less than 2 minutes at 45° C. In addition to Arthrobacter microorganisms of the genus Micrococcus come especially into consideration. It has proven to be particularly advantageous when the microorganism DSM 10239 (BMTU 3346) is used as the enzyme source. DSM 10239 is deposited at the "Deutsche Sammlung für Mikroorganismen und Zellkulturen GmbH", Mascheroder Weg 1b, D-38124 Braunschweig.

The enzyme according to the invention is usually purified below ca. 10° C., advantageously at ca. 4° C. Firstly the cells are disrupted by measures known to a person skilled in the art; this is preferably carried out mechanically by means of a high pressure press or a homogenizer. Subsequently the DNA components are separated e.g. by a Polymin precipitation. For the further purification the supernatant is firstly subjected to a hydroxyapatite chromatography (e.g. hydroxyapatite Ultrogel) which is followed by an anion exchange chromatography (preferably on Q-Sepharose ff high load) and a hydrophobic interaction chromatography. The latter can for example take place on phenyl Sepharose ff.

Details of the purification of the enzyme are as follows:

A certain amount of cells are suspended in the form of their dry weight in a frozen state with a low concentrated substance which buffers well in the pH range of ca. 7.2 to 8.0 such as e.g. phosphate buffer containing an SH reagent. Subsequently the cells are disrupted by incubation with lysozyme; usually 30 minutes at ca. 4° C. are adequate for this. The actual cell disruption is carried out mechanically for example by means of a high pressure press or a homogenizer. Usually a degree of lysis of ca. 30% is achieved.

In order to separate nucleic acid components these are precipitated under non-denaturing conditions. A step-wise precipitation with a dilute Polymin solution has proven to be particularly suitable in this case. After a short incubation phase and centrifugation, the supernatant is advantageously dialysed against the buffer solution which had been used for suspending the biomass. It has turned out that the dialysis is usually completed after ca. 16 hours. The dialysate is separated over a hydroxyapatite Ultrogel column. In every case the appropriate chromatography material is firstly equilibrated with the solution in which the fraction which is to be separated is also present. The fraction containing the enzyme is eluted with a linear gradient of ca. 10 mM to 1 M buffer solution e.g. a phosphate buffer at ca. pH 7.5. The combined fractions are dialysed against a solution buffering at ca. pH 8.0. Tris/HCl and also triethanolamine, N-methyldi-ethanolamine or other organic or inorganic buffers with a buffer capacity between pH 7.8 to 8.4 are suitable as buffers in this case. The combined dialysate is applied to an anion exchanger column equilibrated with this dialysate buffer such as for example Q-Sepharose ff high load and eluted with a linear gradient of increasing concentrations of sodium chloride. The combined eluate fractions are admixed with ammonium sulfate (final concentration: 1.3 M) and applied to a hydrophobic column material. In this case phenyl Sepharose ff has proven to be particularly suitable as the column material. The column material is equilibrated with buffer such as potassium phosphate buffer additionally containing especially ca. 1 M ammonium sulfate. After loading the column material, it is eluted with a linear gradient containing increasing amounts of glycerol at pH ca. 6.0. The fractions having the appropriate enzyme activity are combined and dialysed against a suitable buffer system which contains at least 100 mM sodium chloride and at least 40% glycerol. This dialysis buffer has also proven to be suitable as a storage buffer for the enzyme if the mixture is composed of ca. 10 to 250 mM of a substance buffering in a weak alkaline pH range such as Hepes, Tris or triethanolamine, ca. 0.1 to 5 mM of an organic complexing agent such as EDTA, an agent stabilizing SH groups or reducing SS groups at a concentration of ca. 0.5 to 5.0 mM, 200 to 350 mM sodium chloride and ca. 45 to 55% glycerol. An appropriate mixture containing ca. 300 mM sodium chloride as well as ca. 50% (v/v) glycerol and optionally ca. 0.1 to 5.0 mg/ml bovine serum albumin has proven to be especially advantageous for the storage. The UNG enzyme can be stored in such a buffer between ca. +4° C. and −20° C. for up to one year without a noticeable loss of activity.

The enzyme can be obtained using the process according to the invention with a degree of purity of at least 95% (SDS-PAGE). The enzyme isolated in this way has a specific activity of at least $5 \times 10^4$ units/mg at a temperature optimum of ca. 37° C. and a pH optimum of ca. pH 6.5. The apparent molecular weight of the enzyme is between 23000 and 24000, at Ca. 23400 dalton (SDS-PAGE).

A further advantage of the enzyme according to the invention is that it is almost free of foreign activities. i.e. It was possible to show that relative to the total activity of UNG less than 2% and in many cases less than 0.1% of foreign enzyme activities are present. In particular activities of the following enzymes could not be detected: DNases, nicking activity, single-strand DNAses, RNases and exonucleases.

A further advantage of the UNG enzyme according to the invention is its low heat stability. At ca. 40° C. the half-life of the enzyme is less than 5 minutes whereas when incubated at ca. 45° C. a half-life of approximately 2 minutes or less and often of ca. 60 seconds or less was determined. These stability data were determined in Tris/HCl buffer (pH range 8.3 to 8.9) which additionally contained magnesium chloride and potassium chloride.

The UNG according to the invention is suitable for the detection of DNA containing uracil or for removing the base uracil from DNA in particular from PCR products containing uracil. For this purpose the UNG is placed in a system buffering between pH 7.5 and pH 9.2. In this case buffer systems which are known to a person skilled in the art for use in PCR have proven to be especially suitable (Sambrook, J., Fritsch, E. F., Maniatis, T., Molecular Cloning: A Laboratory Manual, 2nd edition, Cold Spring Harbor Laboratory Press, 1989). In particular inorganic or organic buffers such as for example Tris-HCl in a concentration range of 5 to 100 mM which additionally contain more than 30 mM potassium chloride and ca. 0.5 to 3 mM magnesium chloride have proven to be advantageous. The UNG is preferably at a concentration of ca. 5 to 40 U/ml particularly preferably of ca. 20 U/ml. An incubation of ca. one to 30 minutes at a temperature of ca. 10° C. to 30° C. has proven to be adequate in most cases to degrade contaminating DNA containing uracil. Subsequently the UNG is inactivated by heating it to ca. 95° C. for between ca. 1 and 10 minutes, advantageously for ca. 2 minutes. In this process it has proven to be advantageous that the UNG according to the invention does not have any residual activity after inactivation during a longer incubation (ca. 4° C.) of several hours (ca. 4 h). This property has proven to be particularly advantageous in the so-called carry-over prevention method since the known UNGs e.g. the enzyme obtainable from *E. coli* cannot be as easily inactivated by heat treatment and thus a considerably higher residual activity remains. Moreover, the presence of a lower residual activity after treatment of DNA, for example PCR products, with the enzyme according to the invention is advantageous with regard to an improved or longer storage capability.

The invention in addition concerns a kit (reagent) for amplifying specific nucleic acid fragments and in particular for carrying out PCR under the described improved carry-over-prevention conditions. In addition to the conventional nucleotide triphosphates the kit contains the nucleotide triphosphate dUTP, a thermostable polymerase, the heat-labile UNG according to the invention as well as a suitable reaction buffer. In particular this kit contains the heat-labile UNG at a concentration of 0.1 to 5 U/µl. In addition the kit contains the nucleotide triphosphates dATP, dCTP, dGTP at a concentration of 10 mM as well as the nucleotide triphosphate dUTP at a concentration of 30 mM. In addition the kit contains a buffer for carrying out the decontamination, heat inactivation of the UNG and PCR. This buffer is buffered in a weak alkaline range between pH 7.5 and 9.2 preferably pH 8.3 to 8.9. In this case suitable buffer substances are for example 10 mM Tris/HCl. Moreover the buffer contains ca. 10 to 100 mM KCl (50 mM is preferred), $MgCl_2$ between 1.0 and 5 mM. The polymerase that is preferably used is Taq-DNA polymerase isolated from Thermus aquaticus; the concentration is 2 to 10 U/µl, preferably 5 U/µl.

Thus in summary the heat-labile enzyme according to the invention with uracil-DNA-glycosylase activity is surprisingly more easy to inactivate by heat treatment than known enzymes. In addition it was possible to show that the use of the enzyme according to the invention in the carry-over prevention method exhibits a substantially lower residual activity after carrying out PCR. This leads to a considerable improvement with regard to quantity and quality of the PCR product; in particular since PCR products containing uracil are not degraded after the PCR due to residual activity (and/or reactivation) of the UNG.

Comparison of the heat inactivation of UNG from DSM 10239 and *E. coli*.

In each case 1 U of the UNG from DSM 10239 and *E. coli* was diluted in 100 μl PCR buffer and incubated at 40 and 45° C. At certain times samples were taken and the remaining residual activity was determined.

(-▲- (40° C.), -■- (45° C.): UNG DSM 10239;

(-Δ- (40° C.), -□- (45° C.); UNG *E. coli*).

FIG. 2A:

Determination of the residual activity of UNG after inactivation and PCR.

In each case 2 U of the UNG from DSM 10239 as well as from *E. coli* was added to a PCR mixture. Afterwards the UNG was inactivated for 2 min at 95° C. Subsequently the PCR (amplification with a fragment of 103 base pairs in length) was carried out. After the PCR the sample was cooled to 4° C. Lanes A 1–4 show the experiment of the mixture containing UNG from DSM 10239. Lanes B 1–4 show the corresponding experiment for UNG from *E. coli*, lanes C 1–4 show the control mixtures without UNG. Lanes A1, B1, C1 show the sample for an incubation time T=0; lanes A2, B2, C2 show the sample after an incubation time T=1 h; lanes A3, B3, C3 after 4 hours incubation and lanes A4, B4, C4 after 16 hours incubation. Degradation products of the PCR product are seen for both UNGs after 16 hours. In the case of the UNG from *E. coli* such degradation products already occur at time T=0. Lanes D and E show the time course of the degradation of the PCR products when UNG from DSM 10239 (lane D) and *E. coli* (lane E) are added after the PCR.

Figure 2A:
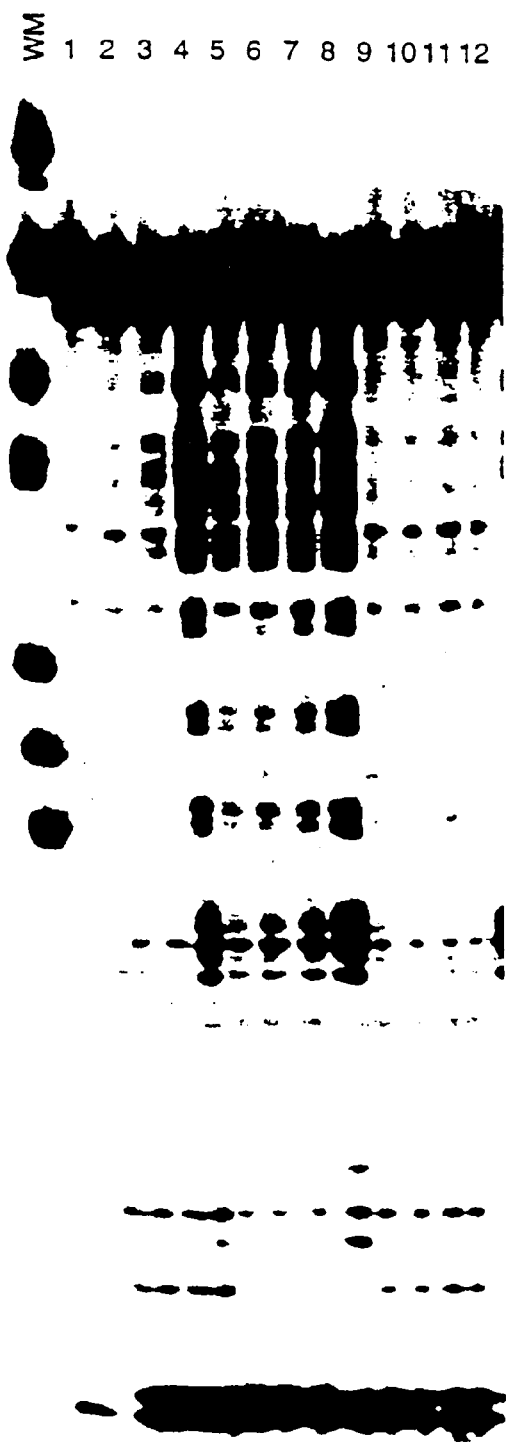

FIG. 2B:

Experimental procedure as in FIG. 2A; however, the inactivation period of the UNG was 10 min at 95° C. Lanes A, B correspond to lanes A, B of FIG. 2A. It can be clearly seen that the UNG from DSM 10239 does not have any degradation products of the PCR fragment in the range between T=0 and T=4 h.

The invention is further elucidated by the following examples:

EXAMPLE 1

Purification of the Heat-labile Uracil-DNA-glycosylase

Definition of the Enzyme Units:

1 U is defined as the amount of uracil-DNA-glycosylase which is required to completely degrade 1 μg of single-stranded DNA containing uracil (bacteriophage M13 grown in *E. coli* CJ236 DUT negative, UNG negative) at 37° C. in 60 min.

Test volumes: 50 μl concentration 60 mM Tris/HCl, pH 8.0; 1 mM EDTA, 1 mM DTT, 0.1 mg/ml BSA.

After incubation for 60 min at 37° C., 16.5 μl M NaOH is added, incubated for 5 min at 37° C., afterwards stopped on ice and subsequently 16.5 μl 0.6 M HCl is added. It is evaluated on a 1% agarose gel.

Purification:

Uracil-DNA-glycosylase is purified at 4° C. The process described here relates to the purification of uracil glycosylase from DSM 10239.

The purification process comprises the following steps:

Disruption of the cells in a high pressure press, Polymin precipitation to separate the DNA, purification of the UNG by chromatography on HA-Ultrogel, anion exchange chromatography (Q-Sepharose ff high load) and hydrophobic interaction chromatography (phenyl Sepharose ff).

Solutions:

Buffer 1: 10 mM potassium phosphate, pH 7.5, 1 mM β-mercaptoethanol

Buffer 2: 10 mM Tris/HCl, pH 8.0/4° C., 1 mM β-mercaptoethanol

Buffer 3: 100 mM potassium phosphate, pH 6.0, 1 M ammonium sulfate, 1 mM β-mercaptoethanol Buffer 4: 100 mM potassium phosphate, pH 6.0, 10% glycerol, 1 mM β-mercaptoethanol Storage buffer: 50 mM Hepes/KOH, pH 8.0, 1 mM EDTA, 1 mM DTT, 300 mM NaCl, 50% glycerol.

40 g Biomass (dry weight) is admixed with 400 ml buffer 1, thawed and suspended. 100 mg lysozyme is added to the suspension and stirred for 30 min at 4° C. Subsequently the cells are disrupted in a high pressure press in two passages. In this process the pressure is 550 kg/cm$^2$. The degree of lysis is usually 20–30% under these conditions.

This is followed by a Polymin precipitation: 10 ml 10% Polymin-p solution is added dropwise. If the precipitation is not complete, Polymin is added again in 2 ml steps in each case. After the titration is completed the precipitate is allowed to stand for ca. 30 min at 4° C. Subsequently the suspension is centrifuged for 30 min at 13,000×g at 4° C. The supernatant of the centrifugation is dialysed (duration 16 h) against a total of 5×5 liter buffer 1. The dialysate is applied to an HA Ultrogel column (2.6×10 cm) equilibrated with buffer 1 and washed with ca. 500 ml buffer 1. Subsequently the enzyme is eluted with a linear gradient of buffer 1 and buffer 1+1 M potassium phosphate pH 7.5 in a total volume of 1.5 l.

The flow rate is 5 ml per minute, the fraction size is 10 ml per fraction.

The enzyme elutes between 50 and 150 mM potassium phosphate. The pooled solutions are dialysed against 4×2 liter buffer 2. The dialysed solution is applied to Q-Sepharose ff high load (2.6×10 cm) equilibrated with buffer 2 and the column is washed with ca. 500 ml buffer 2.

Subsequently the enzyme is eluted with a linear gradient of buffer 2 and buffer 2+1 M NaCl in a total volume of 1.5 liter. The flow rate is ca. 10.0 ml/min, the fraction size is 10 ml.

The enzyme elutes between 200 and 300 mM NaCl concentration.

Solid ammonium sulfate is added to the pooled fractions to a final concentration of 1.3 M while stirring at 4° C. and dissolved. This solution is applied to a phenyl Sepharose ff column (1.6×10 cm) equilibrated with buffer 3. After washing with ca. 200 ml buffer 3 the enzyme is eluted with a linear gradient of buffer 3 and buffer 4 in a volume of 100 ml. The flow rate is ca. 2.5 ml per min, the fraction size is 4 ml. The active fractions are combined and dialysed against storage buffer. The purified UNG is stable in storage buffer between +4° C. and −20° C.

The described method yields a ca. 23.4 kda uracil-DNA-glycosylase in size with a degree of purity of at least 95% (8–25% SDS-PAGE, Phastgel from Pharmacia, Phastgelsystem) and a specific activity of at least 5×10$^4$ units/mg (protein determination by Coomassie). In addition the enzyme is free of contaminating foreign activities (nicking activity, exonuclease and endonuclease).

Determination of Contaminating Foreign Activities:

The test for the presence of contaminating foreign enzyme activities was carried out in a solution composed of 10 mM Tris-HCl, pH 7.5, 10 mM MgCl$_2$, 1 mM DTE. The individual enzyme fractions (20 μl) were incubated with the appropriate nucleic acids. So-called nicking activity was determined by incubation of 1 μg pBR322 for 16 hours at 37° C. Single-stranded and double-stranded nucleases were tested using M13mp9-ss DNA and correspondingly using λ/Eco RI, HindII; the incubation was at 37° C. for 16 hours.

The absence of RNases was tested by incubating the samples with 5 μg MS 2 RNA for 1 hour at 37° C. For the test for exonucleases the samples were incubated for 4 hours at 37° C. with 1 μg [3H]-labelled DNA and the released [3H]-labelled nucleotides were determined.

EXAMPLE 2

Heat-lability of UNG

The heat-lability (ability to be inactivated by heat) of the UNG from DSM 10239 was determined with a radioactive test system.

For this purpose a radioactive test substrate was prepared by random primed labelling. 5 ml Reaction volume contained: 2.5 mg calf thymus DNA, 0.5 μM each of dCTP, dATP, dGTP, 2.6 nM H3-dUTP, 23 nM dUTP, 1 ml hexanucleotide mixture (62.5 OD/ml) and 5 KU Klenow fragment. The reaction mixture was incubated for 1 h at 37° C. Non-incorporated nucleotides were separated by chromatography on Sephadex G50 (2.5×10 cm) (Sephadex G50, equilibrated in 10 mM Tris/HCl, pH 8.0/4° C.). The fractions which contained labelled DNA were collected and concentrated by lyophilization.

Test Procedure:

The test mixture (50 μl) contained 5 μl of the labelled calf thymus DNA (10,000 cpm corresponds to 0.82 pMol H3-uracil), 60 mM Tris/HCl, pH 8.0, 1 mM EDTA, 1 mM DTT, 0.1 mg/ml BSA. After adding UNG at a suitable dilution, the reaction mixture was incubated for 10 min at 37° C.

Subsequently it was terminated on ice, 100 μl precipitation DNA (1 mg/ml) was added and 300 μl 10% trichloroacetic acid (TCA). After a 10 min incubation on ice 4° C.) it was centrifuged for 5 min in a bench centrifuge, 400 μl of the supernatant was used for counting in a scintillation counter.

In the context of the carry-over prevention method UNG is used in a suitable buffer for PCR. The inactivation kinetics of the UNG according to the invention was therefore carried out in a buffer suitable for PCR. The PCR buffer contained 10 mM Tris/HCl, pH 8.3, 1.5 mM MgCl$_2$, 50 mM KCl.

Figure 1:
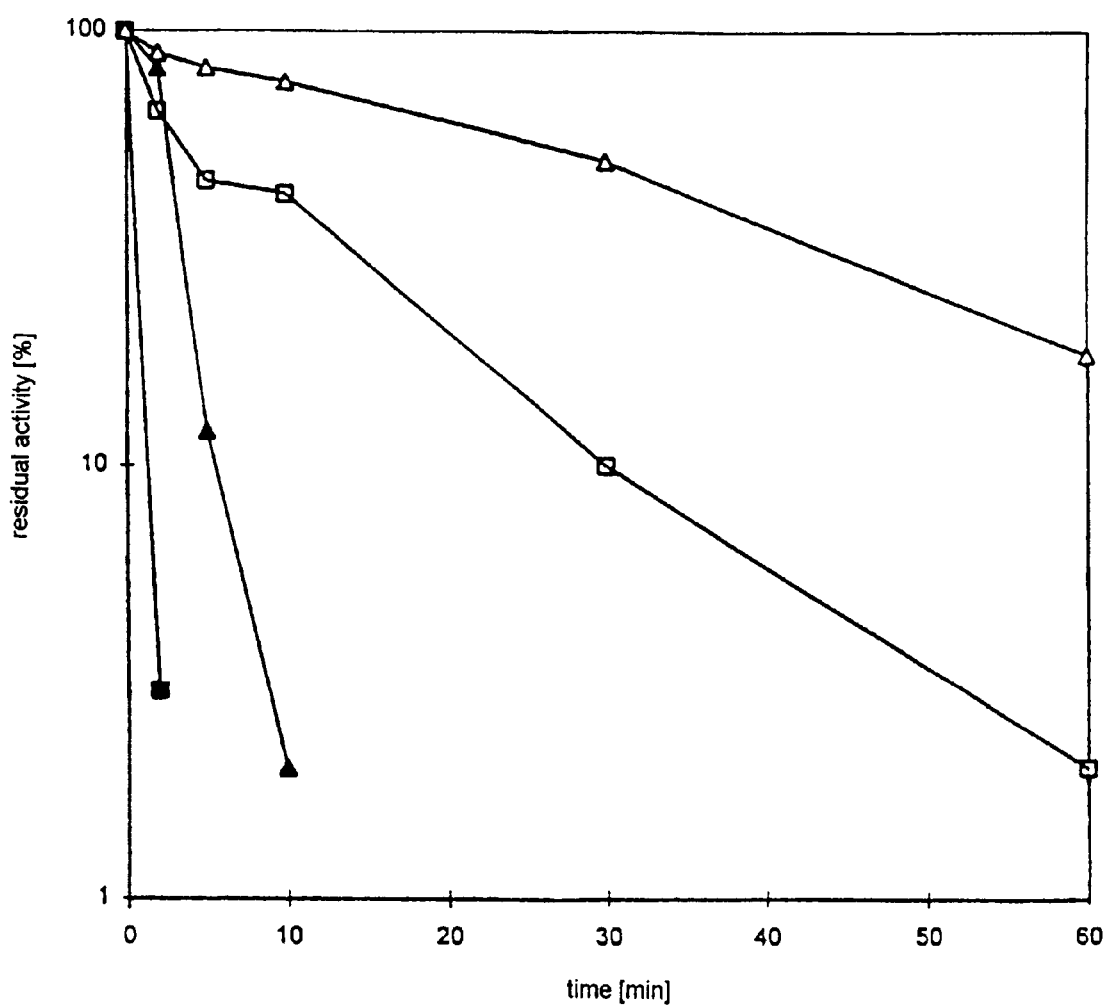
FIG. 1.

1 U UNG was diluted in 100 μl PCR buffer and incubated at various temperatures. Samples were taken at certain times and the remaining residual activity was determined with the test system described above (Table 1). The following half-lives were determined for the UNG according to the invention: 0.5 min at 45° C., 2 min at 40° C. (FIG. 1). In the case of the UNG from *E. coli* the following half-lives were determined: 8 min at 45° C. and 27 min at 40° C.

TABLE 1

| Time [min] | UNG DSM 10239 (40° C.) | UNG DSM 10239 (45° C.) | UNG E. coli (40° C.) | UNG E. coli (45° C.) |
|---|---|---|---|---|
| 0 | 100% | 100% | 100% | 100% |
| 2 | 82% | 3% | 89% | 65% |
| 5 | 12% |  | 82% | 45% |
| 10 | 2% |  | 76% | 42% |
| 20 |  |  |  |  |
| 30 |  |  | 50% | 10% |
| 60 |  |  | 18% | 2% |

EXAMPLE 3

Residual Activity of the UNG According to the Invention after Inactivation and PCR The system described in the following serves to detect residual activity of UNG after heat inactivation and subsequent PCR. In this method the degradation of a PCR product containing uracil is monitored. The PCR product is detected by measuring an incorporated digoxigenin (DIG) label. This labelling was carried out by using a primer labelled with DIG at the 5' end in the PCR; the second primer carries no label. The degradation of the PCR product containing uracil was monitored by detecting the degradation products. The degradation products in this case are separated by means of a sequencing gel and the DIG label is detected via an anti-DIG/chemiluminescence system.

A sequence of 103 base pairs in length from the multiple cloning site of pUC-18 vector was amplified. For this the pUC sequencing 5'-digoxigenin-labelled primer (sequence: 5'-DIG-d[GTAAAACGA CGGCCAGT]-3' (SEQ ID No:1) as well as the pUC reverse sequencing primer (sequence: d[CAGGAAAC AGCTATGAC]-3' (SEQ ID No:2) were used as primers. 100 μl of the mixture contained PCR buffer containing 10 mM Tris/HCl, pH 8.3, 50 mM KCl, 1.5 mM MgCl$_2$; 200 μM of each of the nucleotides dATP, dCTP, dGTP as well as 600 μM dUTP, 2.5 U Taq-DNA polymerase, 1 ng pUC 18-DNA/Pst 1, 2 U UNG and 1 μM of each of the two primers. Afterwards the samples were transferred to a thermo-cycler (e.g. Perkin Elmer 9600). The UNG was heat inactivated within 2–10 min at 95° C. Subsequently PCR is carried out to amplify the 103 base pair fragment. The PCR consists of 25 cycles of 1 min at 94° C., 1 min at 50° C. as well as 3 min at 72° C. Afterwards the sample is stored at 4° C. and samples are taken at suitable time points in order to detect the degradation of the PCR product. 20 μl of the corresponding sample is admixed with 5 μl 0.6 M NaOH, incubated for 5 min at 37° C. and afterwards terminated on ice and subsequently 5 μl 0.6 M HCl as well as 4 μl formamide stopper solution are added. Subsequently the samples are heated for 3 min at 95° C. in order to obtain single strands.

1.5 μl of the sample are applied to an 8% sequencing gel and separated (running time 50 min at 2500 V, 26 mA). The subsequent detection of the DIG-labelled PCR product and of the DIG-labelled degradation products was carried out according to the protocol of the DIG Taq DNA sequencing kit (Boehringer Mannheim) and the DIG luminescence detection kit (Boehringer Mannheim).

FIG. 2A shows the evaluation of such an experiment. In this case the PCR mixtures were stored at 4° C. and samples were taken after 0 h, 1 h, 4 h and 16 h.

Figure 2B:
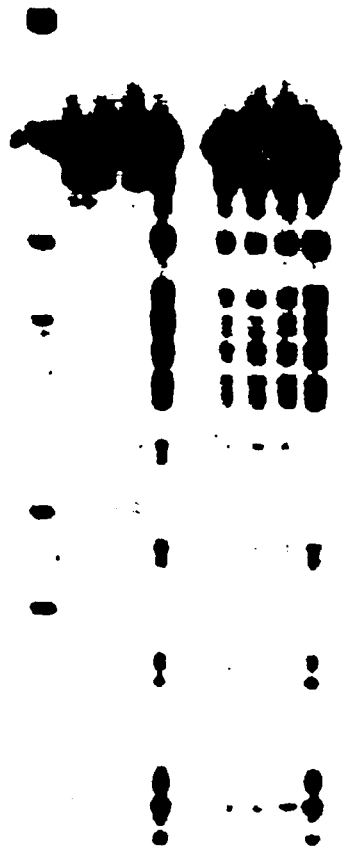
Figure 2B:
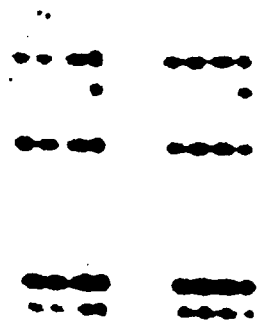

The UNG from *E. coli* (lane B 1–4) is used for a comparison with the UNG from DSM 10239 (lane A 1–4). A mixture without UNG (lane C 1–4) served as a control. In contrast to the *E. coli* UNG hardly any degradation products occurred with the UNG according to the invention at time points 0 to 4 h. Thus with a heat inactivation of 2 minutes at 95° C. the UNG according to the invention exhibits a significant advantage compared to the UNG from *E. coli* (FIG. 2A). The minimal residual activity of the UNG according to the invention can be further decreased by extending the inactivation step (e.g. 10 min at 95° C.) (FIG. 2B).

What is claimed is:

1. A purified enzyme having uracil-DNA-glycosylase activity, a molecular weight between 23,000 and 24,000 daltons and a degree of purity of at least 95% as determined by SDS gel, wherein the enzyme is obtainable from a microorganism of the genus Arthrobacter or the genus Micrococcus, and the enzyme has a half-life of less than 5 minutes at about 40° C. and at most about 2 minutes at about 45° C.

2. The enzyme of claim 1, wherein the enzyme is obtainable from the microorganism DSM 10239.

3. The enzyme of claim 1, wherein the enzyme has a specific activity of at least $5 \times 10^4$ U/mg.

4. The enzyme of claim 1, wherein the enzyme has an optimum uracil-DNA-glycosylase activity at about 37° C.

5. The enzyme of claim 1, wherein the enzyme has an optimum uracil-DNA-glycosylase activity at about pH 6.5.

6. The enzyme of claim 1, wherein the enzyme has a foreign enzyme activity of less than 2%, relative to the uracil-DNA-glycosylase activity.

7. The enzyme of claim 6, wherein the foreign enzyme activity is double-stranded DNase activity, nicking activity, single-stranded DNase activity, RNase activity and exonuclease activity.

8. The enzyme of claim 1, wherein the enzyme has a foreign enzyme activity of less than 0.1%, relative to the uracil-DNA-glycosylase activity.

9. The enzyme of claim 8, wherein the foreign enzyme activity is double-stranded DNase activity, nicking activity, single-stranded DNase activity, RNase activity and exonuclease activity.

10. The enzyme of claim 1, wherein the enzyme has essentially no loss of uracil-DNA-glycosylase activity upon storage in a solution maintained at a temperature of between about +4° C. and −20° C. for up to one year.

11. A solution, comprising an enzyme having uracil-DNA-glycosylase activity and a molecular weight between 23,000 and 24,000 daltons as determined by SDS gel, wherein the enzyme is obtainable from a microorganism of the genus Arthrobacter or the genus Micrococcus and the enzyme has a half-life of less than 5 minutes at about 40° C. and at most about 2 minutes at about 45° C., about 10 to 250 mM of a buffer which brings the solution to a pH of 7.5 to 9.2, about 0.1 to 5 mM of an organic complexing agent, 0.5 to 5 mM of an agent which stabilizes against degradation any SH groups present in the solution, at least 100 mM of sodium chloride and 45 to 55% v/v glycerol.

12. The solution of claim 11, wherein the solution further comprises 0.1 to 5.0 mg/ml bovine serum albumin.

13. The solution of claim 11, wherein the enzyme has essentially no loss of uracil-DNA-glycosylase activity upon storage in the solution maintained at a temperature of between about +4° C. and −20° C. for up to one year.

14. The solution of claim 11, wherein the solution comprises about 50 mM of Hepes/KOH buffer which brings the solution to a pH of about 8.0, about 1 mM of EDTA, about 1 mM of dithiothreitol, about 300 mM of sodium chloride and about 50% v/v glycerol.

15. A process of obtaining a purified enzyme having uracil-DNA-glycosylase activity and a half-life of less than 5 minutes at about 40° C. and at most about 2 minutes at about 45° C., wherein the enzyme has a molecular weight between 23,000 and 24,000 daltons and a degree of purity of at least 95% as determined by SDS gel, the process comprising (a) lysing cells of a gram-positive microorganism to produce a cell lysis mixture comprising the enzyme and nucleic acid;

(b) separating the nucleic acid from the cell lysis mixture to produce a first fraction containing the enzyme;

(c) performing hydroxyapatite chromatography on the first fraction from step (b), to produce a second fraction containing the enzyme;

(d) performing anion exchange chromatography on the second fraction from step (c), to produce a third fraction containing the enzyme; and (e) performing hydrophobic chromatography on the third fraction from step (d), to obtain the purified enzyme.

16. The process of claim 15, wherein the microorganism is of the genus Arthrobacter or the genus Micrococcus.

17. The process of claim 15, wherein the microorganism is DSM 10239.

18. The process of claim 15, wherein the separating step (b) comprises precipitating the nucleic acid with a Polymin solution.

19. The process of claim 15, wherein the anion exchange chromatography of step (d) is carried out on a Q-Sepharose ff high load anion exchange column.

20. The process of claim 15, wherein the hydrophobic chromatography of step (e) is carried out on a phenyl Sepharose ff hydrophobic column.

21. A process for degrading DNA which contains uracil, the process comprising providing a DNA which contains uracil;

incubating an enzyme having uracil-DNA-glycosylase activity and a molecular weight between 23,000 and 24,000 daltons as determined by SDS gel, wherein the enzyme is obtainable from a microorganism of the genus Arthrobacter or the genus Micrococcus and the enzyme has a half-life of less than 5 minutes at about 40° C. and at most about 2 minutes at about 45° C., with the DNA for a time period and at a temperature sufficient to degrade the DNA; and thereafter, inactivating the enzyme by heating the enzyme for a time period and at a temperature sufficient to inactivate the enzyme.

22. The process of claim 21, wherein the DNA is a polymerase chain reaction product.

23. The process of claim 21, wherein the incubating step is carried for a time period of about 1 to about 30 minutes at a temperature of about 10° C. to about 30° C.

24. The process of claim 21, wherein the inactivating step is carried out for a time period of about 1 to about 10 minutes at a temperature of about 95° C.

25. The process of claim 21, wherein the inactivating step is carried out for a time period of at least about 60 seconds at a temperature of at least about 45° C.

26. A reagent suitable for amplifying nucleic acid, comprising
   (a) an enzyme having uracil-DNA-glycosylase activity and a molecular weight between 23,000 and 24,000 daltons as determined by SDS gel, wherein the enzyme is obtainable from a microorganism of the genus Arthrobacter or the genus Micrococcus and the enzyme has a half-life of less than 5 minutes at about 40° C. and at most about 2 minutes at about 45° C.;
   (b) nucleotide triphosphates dATP, dCTP, dGTP and dUTP;
   (c) a thermostable DNA polymerase; and
   (d) a buffer which brings the reagent to a pH of 7.5 to 9.2.

27. The reagent of claim 26, wherein the enzyme is present at a concentration of about 0.1 to 5.0 U/$\mu$l.

28. The reagent of claim 26, wherein each of the nucleotide triphosphates dATP, dCTP, dGTP and dUTP is present at a concentration, and the concentration of each of the nucleotide triphosphates dATP, dCTP and dGTP is about one third of the concentration of the nucleotide triphosphate dUTP.

29. The reagent of claim 26, wherein the thermostable DNA polymerase is present at a concentration of about 2 to 10 U/$\mu$l.

30. The reagent of claim 26, further comprising at least one of about 10 to 100 mM potassium chloride and about 1.0 to 5.0 mM magnesium chloride.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Artificial sequence
<220> FEATURE:
<223> OTHER INFORMATION: Description of Artificial Sequence: synthetic
      oligonucleotide

<400> SEQUENCE: 1
gtaaaacgac ggccagt                                                    17

<210> SEQ ID NO 2
<211> LENGTH: 17
<212> TYPE: DNA
<213> ORGANISM: Artificial sequence
<220> FEATURE:
<223> OTHER INFORMATION: Description of Artificial Sequence: synthetic
      oligonucleotide

<400> SEQUENCE: 2
caggaaacag ctatgac                                                    17